(12) United States Patent
Mahon et al.

(10) Patent No.: US 6,983,066 B2
(45) Date of Patent: Jan. 3, 2006

(54) MACHINE VISION

(75) Inventors: James Mahon, Dublin (IE); Niall Burke, Sallins (IE); Adrian Boyle, Monasterevin (IE); Karl Stanley, Dublin (IE); Brian Farrell, Dublin (IE); Peter Conlon, Dublin (IE)

(73) Assignee: MV Research Limited, Dublin (IE)

( * ) Notice: Subject to any disclaimer, the term of this patent is extended or adjusted under 35 U.S.C. 154(b) by 684 days.

(21) Appl. No.: 10/120,382

(22) Filed: Apr. 12, 2002

(65) Prior Publication Data

US 2002/0114505 A1 Aug. 22, 2002

Related U.S. Application Data

(63) Continuation of application No. PCT/IE00/00130, filed on Oct. 17, 2000.

(30) Foreign Application Priority Data

Oct. 18, 1999 (IE) ...................................... 990870
Nov. 5, 1999 (EP) .................................. 99650103

(51) Int. Cl.
*G06K 9/00* (2006.01)
(52) U.S. Cl. ..................... 382/141; 348/86; 250/492.2; 438/16
(58) Field of Classification Search ........ 382/141–152; 356/237.1–237.6; 348/86–95,125–134; 700/95; 700/ 250/492.2, 493.1–504 R; 29/833; 438/16
See application file for complete search history.

(56) References Cited

U.S. PATENT DOCUMENTS

| 4,692,690 | A |   | 9/1987  | Hara et al. ..................... 327/73 |
| 4,882,498 | A |   | 11/1989 | Cochran et al. ............ 250/571 |
| 5,039,868 | A | * | 8/1991  | Kobayashi et al. ..... 250/559.08 |
| 5,245,671 | A |   | 9/1993  | Kobayashi et al. ............ 382/8 |
| 5,369,492 | A |   | 11/1994 | Sugawara .................... 356/394 |
| 5,713,661 | A |   | 2/1998  | White ......................... 362/355 |
| 5,914,486 | A | * | 6/1999  | Yamamoto ................... 250/226 |
| 5,982,493 | A | * | 11/1999 | Lehnen et al. .............. 356/613 |
| 5,995,220 | A | * | 11/1999 | Suzuki ..................... 356/237.5 |
| 6,135,350 | A | * | 10/2000 | White et al. ................. 235/380 |
| 6,238,060 | B1 | * | 5/2001 | Bourn et al. ................. 362/216 |
| 6,273,338 | B1 | * | 8/2001 | White ................... 235/462.42 |
| 6,529,624 | B1 | * | 3/2003 | Kim ........................... 382/150 |

FOREIGN PATENT DOCUMENTS

| EP | 0443289 A2 | 8/1991 |
| EP | 0452905 A1 | 10/1991 |
| JP | 6-66534 | 3/1994 |
| JP | 7-12748 | 1/1995 |

* cited by examiner

*Primary Examiner*—Bhavesh M. Mehta
*Assistant Examiner*—Aaron Carter

(57) ABSTRACT

An illumination head (1) for machine vision has an annular support (2) with first, second, third, and fourth illumination sections (3, 4, 5, and 6). The third section (5) has three sets of LEDs (12, 13, 14) arranged in a pattern so that each set illuminates at approximately the same angle. Each set is driven in succession so that a series of three monochrome images at the same angle are captured. These are superimposed by an image processor to provide a color image, although the camera is monochrome. More information can be obtained in such a color image and the high resolution and robustness of monochrome cameras is availed of.

16 Claims, 2 Drawing Sheets

MACHINE VISION

This is a continuation of PCT/IE00/00130 filed Oct. 17, 2000 and published in English.

FIELD OF THE INVENTION

The invention relates to illumination of targets and capture of images for inspection of the targets. The targets may, for example, be circuit boards in a surface mount production line, either pre-reflow or post-reflow.

PRIOR ART DISCUSSION

It is well known that colour images provide more detailed information than monochrome images. For example, colour images are generally required for pre-reflow component inspection.

U.S. Pat. No. 5,245,671 (Omron) describes one technique for capturing images. This involves use of three rings of light emitters. Each ring emits one of red, green, and blue colours. The light emitters are mounted so that the light is emitted at different angles so that they converge and combine to provide white light. It appears that this technique is effective at generating good quality colour images for analysis. However, it suffers from the need to use a colour camera. This imposes restrictions on the available resolution and it is also quite expensive.

Japanese Patent Specification No. JP07012748 (Omron) describes a system having multiple cameras and optical filtering to separate images. This arrangement appears to be complex because of the need for multiple cameras and for optical filtering. Japanese Patent Specification No. JP06066534 (Iwaki) describes use of rings of light sources at different angles to successively capture monochrome images with different illumination angles.

Therefore, the invention is directed towards providing an illumination unit and a machine vision inspection head incorporating the unit to provide for improved image quality whereby more information may be gleaned than has heretofore been the case.

SUMMARY OF THE INVENTION

According to the invention, there is provided an illumination unit for a machine vision system, the illumination unit comprising:
means for illuminating a target with monochrome illumination for sufficient time for a camera to capture a monochrome image, and
means for subsequently illuminating the target with a different monochrome illumination at substantially the same angle for sufficient time for a camera to capture a different monochrome image of the same target whereby the sequentially-captured monochrome images may be superimposed by an image processor to provide a colour or near-colour image.

In one embodiment, the unit further comprises means for sequentially illuminating a target with a third monochrome illumination.

In one embodiment, the monochrome illumination wavelengths are red, green, and blue.

In one embodiment, each monochrome illumination means comprises a plurality of light emitting diodes of the same wavelength.

In one embodiment, the diodes are arranged in a ring.

In one embodiment, the diodes of different monochrome illumination means are distributed to provide a similar illumination intensity and distribution for each image.

In another embodiment, the unit comprises a plurality of rings, each ring comprising diodes of all illumination means arranged in a uniform pattern.

In one embodiment, the overall pattern is a pleated pattern when viewed from the target.

In one embodiment, the unit further comprises an additional illumination means.

In one embodiment, the additional illumination means comprises a ring of light emitting diodes mounted to direct light at an angle onto a target which is different from that of the monochrome illumination means.

In a further embodiment, the unit comprises an annular support supporting the monochrome illumination means, and supporting a plurality of additional illumination means for illumination at different angle ranges.

In one embodiment, each additional illumination means emits monochrome illumination.

In one embodiment, an additional illumination means emits ultraviolet light.

In one embodiment, an additional illumination means emits near infra red light.

According to another aspect, the invention provides a machine vision head comprising an illumination unit as defined above, a monochrome camera, and a camera controller comprising means for controlling sequential capture of the successive monochrome images.

According to another aspect, the invention provides a machine vision system comprising a machine vision head as defined above and an image processor comprising means for superimposing the monochrome images.

According to a still further aspect, the invention provides a method of inspecting a target, the method comprising the steps of:
(a) illuminating the target with monochrome illumination;
(b) capturing an image when the target is illuminated with the illumination of step (a);
(c) repeating steps (a) and (b) for each of at least one different monochrome illumination at substantially the same angle until a plurality of monochrome images are captured;
(d) combining the monochrome images to provide a combined image; and
(e) processing the combined image to determine information about the target.

In one embodiment, the target includes wet solder paste and a monochrome illumination is of ultraviolet wavelength.

In another embodiment, the target includes copper leads or tracks and a monochrome illumination is of near infra red wavelength.

In one embodiment, the target includes component leads and solder paste, and the monochrome illuminations include green and blue illuminations.

In the latter embodiment, the method may comprise the further steps of illuminating the target with red wavelength illumination at a different angle and processing the images by measuring the overlap between leads, paste, and pads.

DETAILED DESCRIPTION OF THE INVENTION

BRIEF DESCRIPTION OF THE DRAWINGS

The invention will be more clearly understood from the following description of some embodiments thereof given by way of example only with reference to the accompanying drawings in which.

DESCRIPTION OF THE EMBODIMENTS

Figure 1:
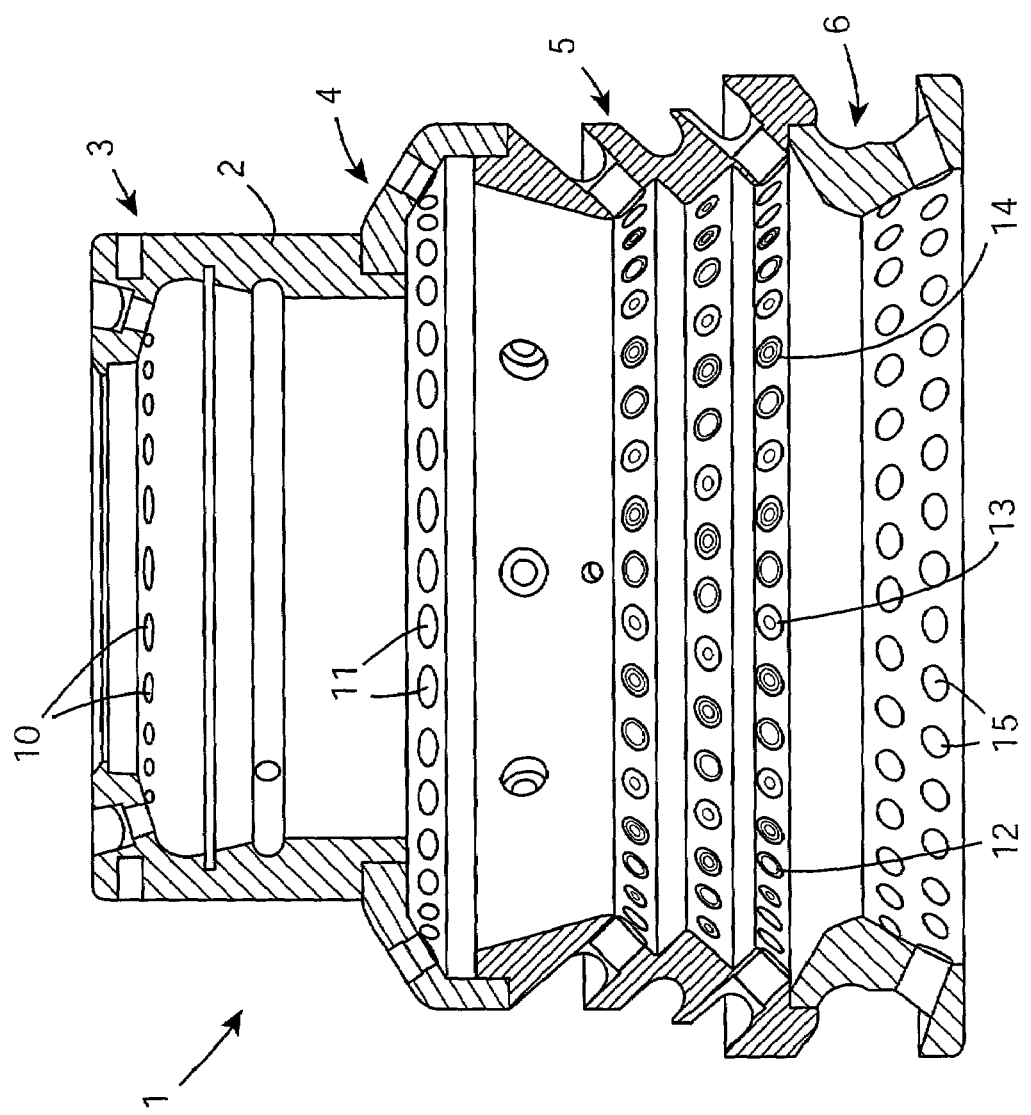
FIG. 1 is a diagrammatic cross-sectional elevational view of an illumination unit of the invention.

Referring to the drawings, an illumination unit 1 of the invention is shown. The unit 1 comprises a support which is generally annular in shape extending in the vertical direction to provide different angles of illumination onto a target. The support 2 comprises, in order from the top down, a first section 3, a second section 4, a third section 5, and a fourth section 6. Each section comprises a wall extending at a different angle to the horizontal so that light emitting diodes (LEDs) mounted on the wall emit at a particular range of angles associated with the section.

In this embodiment, the first section 3 comprises UV LEDs 10 which emit at an angle approximating to 75°. The second section 4 comprises I.R. LEDs 11 which emit at an angle approximating to 60°. The third section 5 comprises LEDs which emit at an angle approximating to 45°. The fourth section 6 comprises red LEDs 15 which emit at an angle approximating to 30°.

The LEDs in the different sections are driven so that a target is illuminated with light at different angles so that different inspection information is obtained. The light wavelength for the sections is chosen for the application. For example, the LEDs in the first section 3 may alternatively be blue, and those in the second section 4 may be red.

The camera used is a monochrome camera. Such cameras provide excellent resolution for relatively little expense.

Figure 2:
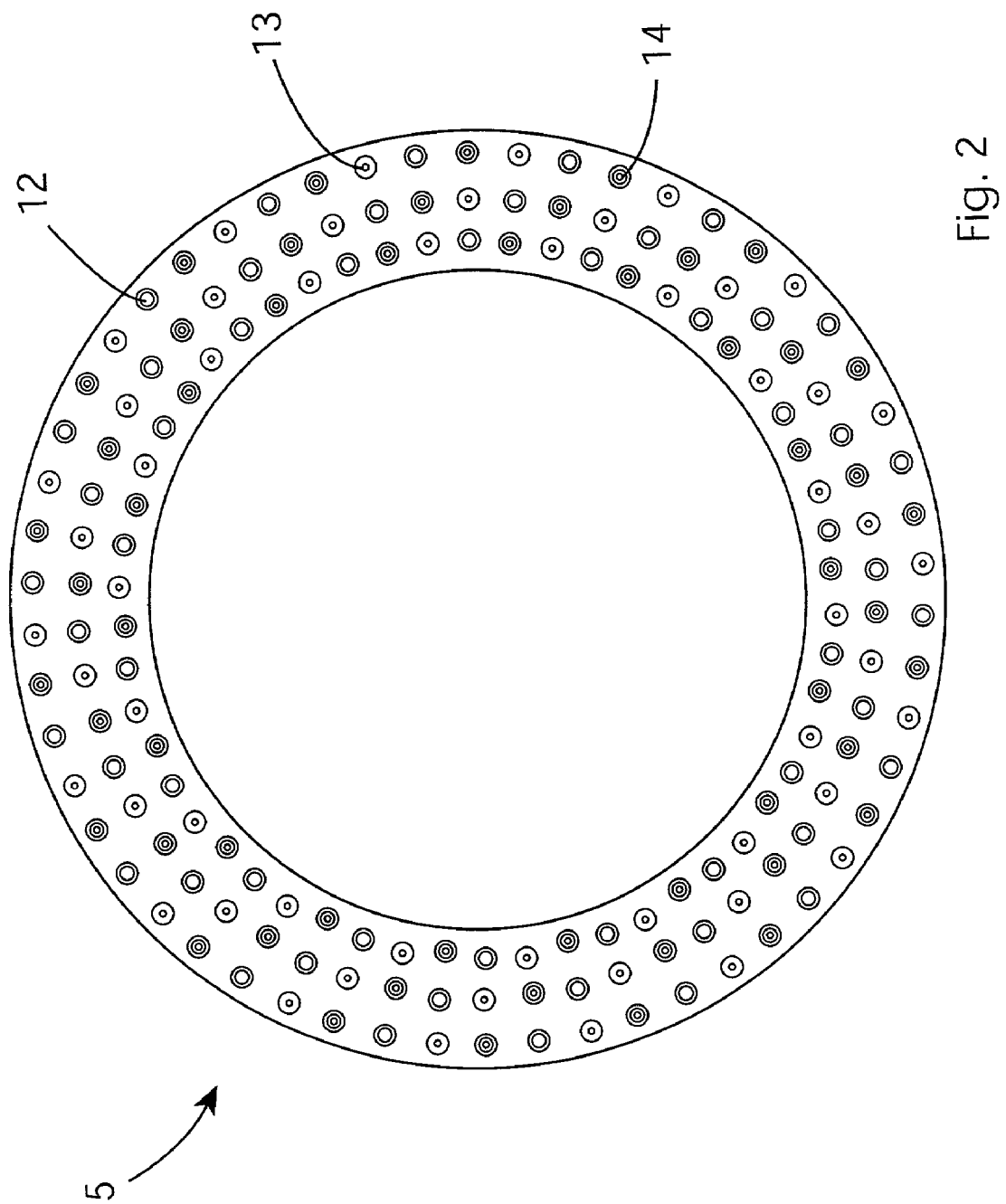
FIG. 2 is an underneath plan view of a section of the unit.

The unit 1 provides for generation of colour images where this is important for inspection analysis. The third section 5 supports three rings of LEDs in close vertical proximity. Each ring within the section 5 comprises blue LEDs 12, red LEDs 13, and green LEDs 14 arranged so that they are interspersed in a uniform pattern around the ring as shown most clearly in FIG. 2. The pattern is very simple and may be expressed as follows:

block position 1: red,
block position 2: green,
block position 3: blue,
block position 4: red,
•
•
•

There may be any suitable number of LEDs in each block, typically ranging from one to ten. This pattern is present in each ring, and it is implemented in each ring so that the colours are offset in adjoining rings in an overall "pleated" pattern for illumination uniformity.

The unit 1 also comprises a drive means, not shown, which activates all blue LEDs 12 in the section 5 for a time period sufficient for the monochrome camera to capture a blue monochrome image. It then activates all of the red LEDs 13 in the section 5 for sufficient time for the camera to capture a red monochrome image while the target is at the same position. Finally, the drive activates all of the green LEDs 14 in the section 5 for sufficient time for the camera to capture a green monochrome image with the target at the same position. For each colour in succession, there is a 5 ms integration followed by an 83 ms image readout time.

Thus, a single high-speed, high-resolution monochrome camera obtains an image for each colour of light by the drive circuit time sequencing the lighting ON with the exposure of the camera for each wavelength of light for which an image is required. Also, further information may be obtained by using the sections 3, 4, or 6. For example, UV LED lighting may be used to stimulate fluorescence or emission at a longer wavelength light that is in the detection band of the sensor. This may further improve classification of scenes.

Returning again to illumination by the section 5, the camera captures three monochrome images of the same target. These are then superimposed by an image processor to provide a colour image. Because the LEDs 12, 13, and 14 are distributed uniformly around the section 5, the illumination intensity and distribution is the same for each monochrome image. Therefore, the colour image generated by the image processor is of excellent quality and at least matches that of a colour camera of the same resolution captured with white light illumination. Indeed, because monochrome cameras are generally available in higher resolution than colour cameras the image quality would be typically better.

Indeed, it has been found that by using multiple monochrome images more information may be obtained than with colour illumination. There are various advantages to use of monochrome illumination and the invention achieves these benefits and the benefits of colour images to obtain the "best of both worlds". In more detail, the resolution, sensor size and speed of monochrome cameras is better. Using a monochrome camera and lighting with different wavelength sources allows sharper and larger images to be obtained as up to 25 mm sensors are available, the pixels are smaller, there is no bleeding of colour, the sensors are of higher quality, and there is no problem with registration of images as all images are taken with the camera/sensor in the same position relative to the object field.

The above is not true of prior art colour CCD cameras or multiple monochrome cameras. Also, an RGB camera is designed to work with white light and to output colour information on the scene. Accordingly, the capability to detect some features is limited as the optimum contrast between these features may occur at a wavelength (or multiple wavelengths) outside the area allowable by the white light/colour sensor combination. The presence of light at a wavelength other than the optimum wavelength for viewing the feature of interest prevents useful information on the scene from being extracted. Also, in the prior art, where optical filtering is used to select the image there is a limit on the number of wavelengths that can be used and the registration between cameras is a problem.

On the other hand, with monochrome cameras made from silicon the CCD sensor has sensitivity for imaging in the 400 nm to 1000 nm wavelength range. Any LED wavelength falling within this range may be used with the monochrome camera and sequential lighting. Using LED switching in the time domain gives greater versatility because some circuit boards may have components that are particularly reflective/transmissive at one wavelength. Using LEDs at the wavelength of interest allows the contrast of the combined images to be maximised by using the spectral reflective and transmissive properties of the region under inspection to be maximised. The section 5 may have LEDs of colours other than red, green, and blue because they may be selected for the particular application. Also, some applications may require only two or greater than three successive illuminations and corresponding images to be merged.

The following are some illustrative examples of applications of the invention.

EXAMPLE 1

Wet Paste Inspection

The Ultraviolet LEDs 10 are used to stimulate fluorescence on particular features so that they may be viewed without distortion from other reflective components. For example, wet solder paste fluoresces visible light when Ultraviolet light is used as illumination. In this case the scene appears as highly bright objects (fluorescent paste) on a black background (UV absorbing solder mask etc). Although metal objects (copper) may reflect the UV this is outside the wavelength selection range of the sensor and so these objects also appear black.

EXAMPLE 2

Copper Inspection

Near Infra red light penetrates the solder mask layer of circuit boards. To inspect copper tracks below the solder mask layer, the Infra red LEDs 11 are used. Switching to the red LEDs 15 in sequence allows the metal outside the solder mask to be viewed and to confirm registration die to the area of bare copper visible under RED lighting. Further inspection of paste on the pads is then possible using the UV LEDs 10 as described in Example 1.

In effect the images under each illumination condition can be used to determine spectral information on the item to be inspected. This may then be used to program the lighting sequence to highlight the contrasts of interest in the identification of particular defects. There is no advantage to using a colour camera to achieve this. Monochrome cameras offer significant advantages to colour cameras for this process.

EXAMPLE 3

Lead to Paste Direct Measurement

Using red LED lighting at angles from the section 6 and using green and blue lighting at one angle from the section 5 it is possible to segment the lead and the paste directly. One can also measure the overlap between the lead, paste, and pad and calculate much more accurately if the part will reflow properly. One can thus reduce the number of "correct but unnecessary" false calls when a part is offset, but could be predicted to reflow properly. This may be possible using a colour CCD also but would require the time sequencing of the lighting to get the contrast required. As a monochrome camera has a bigger sensor (1280×1024 versus 768×576), better resolution, and a higher number of frames per second, it offers significant advantages over a colour camera.

EXAMPLE 4

Paste Under Lead Measurement

The system can detect the presence of paste around leads on pads. If the paste is not present over several adjacent deposits, this can be flagged as an error. The capability to inspect paste when the lead is on top of it is possible because the reflective properties of the lead and paste differ due to selection of lighting conditions that allow specific detection and segmentation of each material. Also, for inspection of a SMT component on a circuit board it is possible to inspect several deposits nearby each other, only calling an error if a certain number of them are bad. Finally, solder bridges between leads may be found using the same lighting configuration.

EXAMPLE 5

Loaded Board Paste and Component Inspection

It is possible to achieve simultaneous 100% component and 100% or nearly 100% paste inspection using illumination from the section 5. This may be used to report paste position as well as presence/absence, to report offsets to the screen printer, and to monitor the forward and backward strokes of the printer. Finally, unpopulated deposits can be used to perform 3D paste measurement if required.

Colour cameras alone would not provide the capability to perform the inspections outlined above. It is achieved in the invention by time sequencing the lighting at each wavelength of interest. Each image is effectively monochrome, and the monochrome images are identified by the lighting source which formed them and the features they contain relative to other monochrome images taken with other lighting on the same camera. However, where desired, sequencing of the red, blue, and green LEDs of the section 5 achieves a colour image when the monochrome images are superimposed.

The invention is not limited to the embodiments described, but may be varied in construction and detail. For example, it is not essential that the unit have additional illumination means to provide illumination at different angles. However, the arrangement described is particularly versatile as it may be used very effectively for both pre-reflow and post-reflow inspection. Also the LEDs in the section 5 may be distributed in a different pattern which achieves sufficiently uniform illumination for all of the sequential images. The benefits from capturing successive monochrome images may be obtained by using more than one camera. If multiple cameras are used, they may be mounted at different angles with respect to the target.

The invention is not limited to the embodiments described but may be varied in construction and detail.

What is claimed is:

1. An illumination unit for a machine vision system, the illumination unit comprising:
    means for illuminating a target with monochrome illumination for sufficient time for a camera to capture a monochrome image,
    means for subsequently illuminating the target with a different monochrome illumination at substantially the same angle for sufficient time for a camera to capture a different monochrome image of the same target whereby the sequentially captured monochrome images are superimposed by an image processor to provide a colour or near colour image,
    wherein each monochrome illumination means comprises a plurality of light emitting diodes of the same wavelength,
    wherein the diodes are arranged in a ring, and
    wherein the diodes of different monochrome illumination means are distributed to provide a similar illumination intensity and distribution for each monochrome image.

2. The illumination unit as claimed in claim 1, wherein the unit further comprises means for sequentially illuminating a target with a third monochrome illumination.

3. The illumination unit as claimed in claim 2, wherein the monochrome illumination wavelengths are red, green, and blue.

4. The illumination unit as claimed in claim 1, wherein the unit comprises a plurality of rings, each ring comprising diodes of all illumination means arranged in a uniform pattern.

5. The illumination unit as claimed in claim 4, wherein the overall pattern is a pleated pattern when viewed from the target.

6. An illumination unit for a machine vision system, the illumination unit comprising:
    means for illuminating a target with monochrome illumination for sufficient time for a camera to capture a monochrome image,
    means for subsequently illuminating the target with a different monochrome illumination at substantially the same angle for sufficient time for a camera to capture a different monochrome image of the same target whereby the sequentially captured monochrome images are superimposed by an image processor to provide a colour or near colour image,
    wherein the unit further comprises an additional illumination means, and
    wherein the additional illumination means comprises a ring of light emitting diodes mounted to direct light at an angle onto a target which is different from that of the monochrome illumination means.

7. The illumination unit as claimed in claim 6, wherein the unit comprises an annular support supporting the monochrome illumination means and supporting a plurality of additional illumination means for illumination at different angle ranges.

8. The illumination unit as claimed in claim 6, wherein each additional illumination means emits monochrome illumination.

9. The illumination unit as claimed in claim 6, wherein an additional illumination means emits ultraviolet light.

10. The illumination unit as claimed in claim 6, wherein an additional illumination means emits near infra red light.

11. A machine vision head comprising an illumination unit as claimed in claim 1, a monochrome camera, and a camera controller comprising means for controlling sequential capture of the successive monochrome images.

12. A machine vision system comprising a machine vision head as claimed in claim 11 and an image processor comprising means for superimposing the monochrome images to provide a colour image.

13. A method of inspecting a target, the method comprising the steps of:
    (a) illuminating the target with monochrome illumination;
    (b) capturing an image when the target is illuminated with the illumination of step (a);
    (c) repeating steps (a) and (b) for each of at least one different monochrome illumination at substantially the same angle until a plurality of monochrome images are captured;
    (d) combining the monochrome images to provide a combined image; and
    (e) processing the combined image to determine information about the target,
    wherein the target includes wet solder paste and an additional illumination means emits illumination of ultraviolet wavelength to stimulate fluorescence in the paste.

14. A method of inspecting a target, the method comprising the steps of:
    (a) illuminating the target with monochrome illumination;
    (b) capturing an image when the target is illuminated with the illumination of step (a);
    (c) repeating steps (a) and (b) for each of at least one different monochrome illumination at substantially the same angle until a plurality of monochrome images are captured;
    (d) combining the monochrome images to provide a combined image; and
    (e) processing the combined image to determine information about the target,
    wherein the target includes copper leads or tracks and an additional illumination means emits illumination of near infra red wavelength to penetrate a solder mask.

15. A method of inspecting a target, the method comprising the steps of:
    (a) illuminating the target with monochrome illumination;
    (b) capturing an image when the target is illuminated with the illumination of step (a);
    (c) repeating steps (a) and (b) for each of at least one different monochrome illumination at substantially the same angle until a plurality of monochrome images are captured;
    (d) combining the monochrome images to provide a combined image; and
    (e) processing the combined image to determine information about the target,
    wherein the target includes component leads and solder paste, and the monochrome illuminations include green and blue illuminations.

16. The method as claimed in claim 15, wherein the method comprises the further steps of illuminating the target with red wavelength illumination at a different angle and processing the images by measuring the overlap between leads, paste, and pads.

* * * * *